United States Patent
Nah et al.

(10) Patent No.: US 10,568,931 B2
(45) Date of Patent: Feb. 25, 2020

(54) PHARMACEUTICAL COMPOSITION COMPRISING GINSENG EXTRACTS FOR PREVENTION AND TREATMENT OF OPHTHALMOLOGICAL DISEASES

(71) Applicant: GINTONIN KU BIOTECH Co., Ltd., Daejeon (KR)

(72) Inventors: Seung-Yeol Nah, Seoul (KR); Joon-Young Kim, Seoul (KR); Hyeon-Joong Kim, Seoul (KR); Seok-Won Jung, Seoul (KR)

(73) Assignee: GINTONIN KU BIOTECH CO., LTD., Daejeon (KR)

( * ) Notice: Subject to any disclaimer, the term of this patent is extended or adjusted under 35 U.S.C. 154(b) by 247 days.

(21) Appl. No.: 15/453,417

(22) Filed: Mar. 8, 2017

(65) Prior Publication Data

US 2018/0256677 A1    Sep. 13, 2018

(51) Int. Cl.
*A61K 36/258* (2006.01)
*A61K 38/16* (2006.01)

(52) U.S. Cl.
CPC .......... *A61K 38/168* (2013.01); *A61K 36/258* (2013.01); *A61K 2236/30* (2013.01); *A61K 2236/33* (2013.01); *A61K 2236/39* (2013.01)

(58) Field of Classification Search
None
See application file for complete search history.

(56) References Cited

U.S. PATENT DOCUMENTS

2009/0317496 A1 * 12/2009 Park ..................... A61K 36/258
424/728

FOREIGN PATENT DOCUMENTS

| KR | 10-2011-0133275 A | 12/2011 |
| KR | 10-2013-0013066 A | 2/2013 |
| KR | 10-2013-0030729 A | 3/2013 |
| KR | 10-2013-0062487 A | 6/2013 |

OTHER PUBLICATIONS

Kim et al. (2017) J. Vet. Sci. 18(3): 387-397. (Year: 2017).*
Cho et al. (2014) Journal of Translational Medicine, 12: 283— (Year: 2014).*
Choi et al. (2011) J. Ginseng Res. vol. 35, No. 4, 471-478. (Year: 2011).*
Choi et al. (2015) J. Ginseng Res. 39: 398-405. (Year: 2015).*
Choi et al. (2015) Front. Pharmacol. 6: 245. (Year: 2015).*
Huynh et al. (2013) Evidence-Based Complementary and Alternative Medicine (Year: 2013).*
Im et al. (2013) Acta Phamacologica Sinica 34: 1367-1373. (Year: 2013).*
Pyo et al. (2011) J. Ginseng Res. vol. 35, No. 2, 209-218. (Year: 2011).*
Raskin et al. (2004) Current Phamraceutical Design, 10: 3419-3429. (Year: 2004).*
Revilla et al. (1998) J. Agric. Food Chem. 46, 4592-4597. (Year: 1998).*
Ke-Ping Xu et al. "Lysophosphatidic Acid Promoting Corneal Epithelial Wound Healing by Transaction of Epidermal Growth Factor Receptor" IOVS, vol. 48, No. 2, pp. 636-643 (Feb. 2007).
Padma Lyer et al. "Autotaxin-Lysophosphatidic Acid Axis Is a Novel Molecular Target for Lowering Intraocular Pressure," PLOS One, vol. 7, Issue 8 (Aug. 2012).

* cited by examiner

*Primary Examiner* — Russell G Fiebig
(74) *Attorney, Agent, or Firm* — Novick, Kim & Lee, PLLC; Sang Ho Lee; Jae Youn Kim (57) ABSTRACT

Provided is a treatment composition for damage treatment and regeneration promotion of corneal epithelial cells containing gintonin as an active ingredient which is glycolipoprotein or its aggregate isolated from ginseng. Since the gintonin as a drug containing high-concentration LPA has an effect of increasing the concentration of LPA in damaged cornea and inducing the proliferation of corneal epithelial cells to rapidly and significantly restore the damage of the cornea, the composition of the present disclosure can be usefully used as drugs for treatment of corneal erosion and corneal ulcer or equivalent therapeutic agents for corneal injury in humans and animals.

7 Claims, 9 Drawing Sheets
(7 of 9 Drawing Sheet(s) Filed in Color)

14-year-old, corneal erosion, using gintonin 9-year-old, corneal erosion, without using gintonin

FIG. 6

Slit lamp microphotograph     Fluorescein staining photograph

A. 13-year-old, corneal erosion, using gintonin

B. 5-year-old, corneal erosion, without using

FIG. 9

PHARMACEUTICAL COMPOSITION COMPRISING GINSENG EXTRACTS FOR PREVENTION AND TREATMENT OF OPHTHALMOLOGICAL DISEASES

STATEMENT REGARDING PRIOR DISCLOSURES

Let it be known that Korean patent application No. 10-2014-0114410 filed on Aug. 29, 2014, and its Korean patent publication No. 10-2016-0026256 published on Mar. 9, 2016, does not apply as prior art to the present application under AIA 35 U.S.C. § 102(b)(1)(A). Furthermore, this prior disclosure is hereby incorporated by reference it its entirety.

TECHNICAL FIELD

The present disclosure relates to a composition for prevention or treatment of ophthalmological diseases containing, as an active ingredient, gintonin which is glycolipoprotein isolated from ginseng.

BACKGROUND

Eyes of animals including humans play an important role in information transfer through the perception of peripheral information. That is, accurate images for a peripheral environment are continuously received through the eyes and information receiving the images is processed in the brain, and thus various functions inducing behaviors appropriate to the situation are performed. Like other organs in the body, a variety of diseases also occur in the eyes. The most common eye disease is keratitis, and includes glaucoma, cataracts and retinal disease. Particularly, scarring caused by corneal ulcer is a major cause of blindness and vision loss worldwide. This vision loss can be prevented by diagnosis of the cause and proper treatment (Vaughan General ophthalmology, 15/e professors of department of Ophthalmology, National Academy of Medicine). In addition, if the corneal ulcer is not treated rapidly but continued for a long time, a scar tissue is formed on the cornea, and new blood vessels enter the cornea, and as a result, transparency of the cornea is deteriorated and astigmatism may occur. Therefore, even after the corneal ulcer is treated, a persistent poor result in the vision may occur. Therefore, the treatment of corneal ulcer is an important therapeutic goal to treat the ulcer as soon as possible.

Alternatively, recently, for vision correction, a refractive corneal surgery using an excimer laser has been frequently performed. A method of cutting parenchymal cells of the cornea using an excimer laser is largely divided into lasik or lasek according to a method of peeling epithelial cells of the cornea. In the surgery, a scar tissue and the like that may remain very finely in the cornea after the vision correction surgery due to damage to corneal epithelial cells and damage to a part of the upper corneal parenchymal cells may affect postoperative pain and complications. Therefore, a rapid healing method of the corneal epithelial cells is a study field which is very importantly considered. In addition, in various ophthalmic procedures, protecting and rapidly regenerating the corneal epithelial cells may ultimately be an important part of effective eye treatment.

In current clinics or veterinary clinics, in order to promote recovery according to corneal injury caused by various factors, platelet rich plasma (PRP) and plasma protein-removed components have been developed and used, but it is not yet known which component plays the role. Glycerol- and sphingosine-based phospholipids are very abundant in the cell membrane and mainly structural components configuring the membrane. Further, these components are also present in the blood, and some components through metabolic processes form lysophospholipids (Okudaira et al., Biochimie 92, 698-706. 2010).

In the lysophospholipids, lysophosphatidylcholine (LPC) is included and receives an action of an enzyme of lysophospholipase D known as autotaxin to generate lysophosphatidic acid (LPA; 1- or 2-acyl-sn-glycerol-3-phosphate) (Aoki, Seminars Cell & Dev. Biol. 15, 477-489, 2004; Okudaira et al., Biochimie 92, 698-706. 2010). It is reported that in the early stage, the LPA is known to be produced when the platelets are activated and associated with hemostasis, wound healing, and tissue regeneration, but according to recent studies, it is known that the LPA is present in plasma, serum, saliva, seminal fluid, follicular fluid, and the like in addition to the platelets and is present at concentrations of 80 to 100 nM in the plasma and 1 to 5 M in the serum (Aoki, Seminars Cell & Dev. Biol. 15, 477-489, 2004). Further, it has also been found that the LPAs are widely distributed in a variety of cells such as adipocytes, fibroblasts, brain, and various organs (Pages et al., Prostaglandins 64, 1-10, 2001).

The LPA present in blood when binding primarily to plasma proteins (e.g., albumin) is more stable, and while the LPA is bound to the plasma proteins (mainly, albumin) and circulated with the plasma protein when the blood is circulated, the LPA is bound to a LPA receptor in a target organ to exhibit the effect (Croset et al., Biochem J 345, 61-67, 2000). A phosphate group and a glycerol backbone of the LPA play an important role in LPA action (Jalink et al., Biochem J. 307, 609-615, 1995). Although the LPA in which the phosphate group is present in the blood is present at 1 to 5 M, since the phosphate group of LPA is removed by an enzyme called lysophospholipid phosphatase in the blood or the cell membrane in a very short time and the LPA is inactivated, many studies on synthesis or development of LPA analogs which are not easily metabolized and works for a long time under the influence of enzymes have been conducted, but compounds suitable for clinical applications are not yet found (Pilquil et al., Prostaglandins. 64, 83-92, 2001; Brindley and Pilquil, J Lipid Res. 50 Suppl S225-230, 2009; Croset et al., Biochem J 345. 61-67, 2000; Deng et al., Gastroenterology 132. 1834-1851, 2007). It is expected that the protein component of gintonin serves to as stabilizer that protect and stabilize the LPAs.

SUMMARY

The present researchers recognized that LPA was involved in recovery of ophthalmological diseases, particularly, corneal diseases caused by various factors and developed a therapeutic agent for corneal injury by using features of gintonin. Further, the present researchers found that as in vivo studies using rabbits and studies on the therapeutic efficacy of dogs with ophthalmological diseases in veterinary hospitals, gintonin had excellent efficacy inducing rapid treatment of corneal injury of the eye or keratitis as eye infection as compared with conventional used drugs and completed the present disclosure.

Therefore, the present disclosure has been made in an effort to provide a composition for prevention or treatment of ophthalmological diseases, containing gintonin as an active ingredient.

Further, the present disclosure has been made in an effort to provide health functional food for improvement of ophthalmological diseases, containing gintonin as an active ingredient.

Further, the present disclosure has been made in an effort to provide a method for treatment of ophthalmological diseases of animals except for humans, including treating eyeballs with gintonin.

Further, the present disclosure has been made in an effort to provide a method for treatment of injury of keratocytes, including treating keratocytes with gintonin in vitro.

Further, the present disclosure has been made in an effort to provide a method for preparing a composition for prevention or treatment of ophthalmological diseases containing gintonin as an active ingredient, including preparing an alcohol extract by adding alcohol to ginseng powder; collecting the alcohol extract by using an anion-exchange resin; and fractioning the collected extract by a dialysis membrane having pore sizes of 6,000 to 8,000.

An exemplary embodiment of the present disclosure provides a composition for prevention or treatment of ophthalmological diseases, containing gintonin as an active ingredient.

The gintonin may be a glycolipoprotein isolated from ginseng.

The gintonin may be extracted by selecting one or more of water, ethanol, methanol, and butanol as a solvent.

The gintonin may be gintonin obtained by removing a low molecular material using an anion-exchange resin.

The ginseng may be one or more selected from the group consisting of roots, leaves, stems, fruits, and flowers of the ginseng.

The ginseng may be one or more selected from the group consisting of red ginseng, fresh ginseng, white ginseng, cultivated ginseng, *panax ginseng*, wild ginseng, and ginseng and red ginseng byproducts.

The ginseng may be one or more selected from the group consisting of *Panax ginseng, P. quiquefolius, P. notoginseng, P. japonicus, P. trifolium, P. pseudoginseng, P. vietnamensis*, and *Panax quinquefolium*.

The gintonin may have a concentration of 125 to 1000 μg/ml.

The gintonin may have a concentration of 250 to 750 μg/ml.

The composition may be an eye liquid or injection.

The ophthalmological diseases may be selected from the group consisting of corneal diseases, xerophthalmia, conjunctivitis, trachoma, episcleritis, uveitis, glaucoma, cataract, macular degeneration, myodesopsia, retinal vascular occlusions, haemorrhagia corporis vitrei, retinal detachment, and central retinosis.

The corneal disease may be corneal erosion, corneal ulcer, or corneal injury.

The gintonin may activate LPA receptors in cells.

The gintonin may increase a concentration of free calcium ($Ca^{2+}$) in the cytoplasm.

Another exemplary embodiment of the present disclosure provides health functional food for improvement of ophthalmological diseases, containing gintonin as an active ingredient.

Yet another exemplary embodiment of the present disclosure provides a method for treatment of ophthalmological diseases of animals except for humans, including treating eyeballs with gintonin.

Still another exemplary embodiment of the present disclosure provides a method for treatment of injury of keratocytes, including treating keratocytes with gintonin in vitro.

The keratocytes may be human corneal epithelial cells.

Still yet another exemplary embodiment of the present disclosure provides a method for preparing a composition for prevention or treatment of ophthalmological diseases containing gintonin as an active ingredient, including preparing an alcohol extract by adding alcohol to ginseng powder; collecting the alcohol extract by using an anion-exchange resin; and fractioning the collected extract by a dialysis membrane having pore sizes of 6,000 to 8,000.

The alcohol extract may be extracted by reflux cooling.

According to the exemplary embodiment of the present disclosure, the gintonin isolated from the ginseng of the present disclosure efficiently heals corneal injury and treats keratitis, conjunctivitis, episcleritis, uveitis, and the like due to infection by a mechanism of rapidly regenerating cells damaged by various factors to exhibit a normal function of the eyes.

Further, the gintonin contains a lot of glycolipoproteins and has therapeutic effects such as xerophthalmia, macular degeneration, myodesopsia, and the like, and may be useful used in humans or animals as medicines for the treatment of glaucoma, cataract, retinal vascular occlusion, vitreous hemorrhage, retinal detachment, and central retinosis through the regulation of calcium channel.

The foregoing summary is illustrative only and is not intended to be in any way limiting. In addition to the illustrative aspects, embodiments, and features described above, further aspects, embodiments, and features will become apparent by reference to the drawings and the following detail description.

BRIEF DESCRIPTION OF THE DRAWINGS

The patent or application file contains at least one drawing/photograph executed in color. Copies of this patent or patent application with color drawing(s)/photograph(s) will be provided by the Office upon request and payment of the necessary fee.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here. The present disclosure is characterized by using a composition containing gintonin as an active ingredient in ophthalmological diseases.

In the related art, there are various therapeutic agents in ophthalmological diseases, but in the ophthalmological diseases, there are problems in that the causes thereof are unclear, the most of treatment is symptomatic treatment, a lot of time in treatment is required, and thus eyesight is deteriorated after treatment.

Therefore, the present inventors found that when the composition containing the gintonin is treated in cells related with the eyes, the injured cells are rapidly regenerated and aftereffects may be minimized at the same time.

In the present disclosure, the gintonin is a glycolipoprotein isolated from the ginseng or aggregates thereof, and the present inventors verified that in a recent study, features of the ginseng in the related art are caused by a glycolipoprotein consisting of proteins other than ginsenoside, carbohydrates and fats, purified and identified the glycolipoprotein from the ginseng, and named the glycolipoprotein as gintonin (see Korean Patent Application No. 2009-0110662).

Further, in the related art, a method of preparing gintonin which is a novel glycolipoprotein includes the steps of: (1) preparing a methanol extract from ginseng; (2) fractioning the methanol extract with a mixed solvent of water and n-butanol; (3) isolating the n-butanol fraction of the water fraction and the n-butanol fraction into 8 fractions by performing silica gel column chromatography using a mixed solvent of chloroform:methanol:water as an eluting solvent; (4) isolating the 7-th fraction having the highest activity for $Ca^{2+}$-activated chloride channel (CaCC) of 8 fractions into two fractions by performing silica gel column chromatography using a mixed solvent of ethanol:ethylacetate:water as an eluting solvent; and (5) dialyzing the fraction having higher CaCC activity of the two fractions to obtain final product (Korean Patent Registration No. 10-0973202).

In the present application, the ginseng may be one or more selected from the group consisting of roots, leaves, stems, fruits, and flowers of the ginseng and all of red ginseng, fresh ginseng, white ginseng, cultivated ginseng, *panax ginseng*, wild ginseng, and ginseng and red ginseng byproducts may be used. Particularly, the ginseng may use *Panax ginseng, P. quiquefolius, P. notoginseng, P. japonicus, P. trifolium, P. pseudoginseng, P. vietnamensis*, or *Panax quinquefolium* and is not limited to a kind of ginseng.

In the present application, the ophthalmological diseases or the eye diseases mean diseases caused by retina, cornea, conjunctiva, uveal tract, anterior segment or posterior segment, glaucoma, cataract, and the like.

Keratitis is a disease in which inflammation in the cornea occurs to cause pain, redness, decreased vision, corneal opacity, and the like, and xerophthalmia means an eye disease in which due to the lack of tears, excessive evaporation of tears, or unbalance of tear components, the eye surface is damaged, the eyes are irritated, and irritation symptoms such as irritation, foreign body sensation, and dryness are felt.

Corneal injury means all diseases or injuries that cause damage to transparent eyesight due to damage to the cornea, and corneal ulcer means that when the cornea, which is the transparent tissue at the anterior part of the eye, is damaged, inflammation is caused by bacteria, viruses, fungi or various causes, and thus, a part of the cornea is dented. Further, corneal erosion (alternatively, referred to as corneal epithelial detachment and corneal epithelial erosion) is caused by mechanical and chemical trauma and most of corneal erosion is frequently caused by edematous inflammation and degenerative disease. A part of the epithelial detachment is involved in a cloudy turbidity and tissue loss may be determined visually or not be determined without microscope-dependency. When a drop of 0.2% fluorescein is dropped in the eyes and a blue filter is applied, the fluorescein is not absorbed in the normal epithelium, but input in a lost or damaged part to emit yellow fluorescence.

Conjunctiva is a tissue covering the eyes (eyeballs) from the outside, infectious conjunctivitis is caused by infection with various pathogens such as bacteria, viruses, and mycete (fungi), and noninfectious conjunctivitis is caused by noninfectious factors, such as allergic conjunctivitis, which is caused by an allergic reaction to foreign substances.

The uvea means the iris that forms the middle layer of the eyeball (a brown tissue inside the cornea called the black part of the eye ball when seen from the front of the eye), the ciliary body, and the choroids, and inflammation that occurs in the uvea is referred to as uveitis.

Glaucoma is a disease in which the optic nerve is pressed by the elevation of the intraocular pressure or abnormality in the optical nerve function is caused by disorder of the blood supply, and cataract is a disease in which the lens becomes hazy and does not pass the light properly and thus the field of vision becomes cloudy like the fog.

In treatment of acute glaucoma, it is important to preserve the optic nerve by quickly dropping the intraocular pressure. First, the intraocular pressure is quickly dropped through treatment such as applying eye drops decreasing the intraocular pressure in the eyes, taking ocular hypotensive agent through the mouth, and administering a hyperosmotic agent through intravenous injection, and the like. After the intraocular pressure is dropped, small holes are pierced in the iris by using a laser to help water circulation and discharge. Further, in chronic glaucoma, in order to prevent any more optic nerve damages, the ocular hypotensive agent is applied in the eyes and if one drug has no effect, various series of drugs are used.

The nerve tissue located in the center of the inner retina of the eye is called the macula, and most of optic cells are concentrated here, and the places where the image of the object is formed is also the center of the macula, so it plays a very important role in eyesight. A disease that degeneration of the macula is caused by various causes to cause visual impairment is referred to as macular degeneration. In addition, retinal vascular occlusion is a symptom of visual loss due to clogging of the blood vessels flowing through the retina and central retinosis is a symptom of causing fluid due to damage to the retina.

Most of myodesopsia is caused by a change in the vitreous body (or hyaloid body) with increasing age.

In the present disclosure, the LPA means lysophosphatidic acid and is lysophosphatide in which 2-position acyl group of phosphatidic acid is released to be a hydroxyl group. The LPA has large water solubility, and is a first intermediate in the de novo synthesis of phosphatide from glycerol-3-phosphate and then rapidly transformed into phosphatidic acid, and as a result, only trace amounts exist in vivo. The LPA receives attention as a bioactive lipid which is made in response to stimuli in platelets and the like, has a hyperactivity action on cultured fibroblasts, has a possibility of presence of a specific receptor to a cell membrane. Further, lysophosphatidic acid, which is one of lipid mediators as the receptor, is known to activate an information transfer pathway that interacts with a G protein and recently, two kinds of receptor genes have been verified. Vzg-1 cloned in immortal mouse neurons is a homologous gene of Edg-2 identified as a mouse endothelial cell differentiation gene and activates an information transfer system connected to a Gi protein and a G12/13 protein.

The composition of the present disclosure may include a therapeutically effective amount of a cell therapeutic agent for treatment of diseases. The term "therapeutically effective amount" means an amount of an active ingredient or a pharmaceutical composition which induces a biological or medical response in a tissue system, an animal, or the human which is considered by researchers, veterinarian, physician, or other clinicians, and includes an amount of inducing alleviation of symptoms of diseases or disorders to be treated. It is obvious to those skilled in the art that the gintonin included in the composition of the present disclosure is changed according to a desired effect. Therefore, the optimal content of the gintonin may be easily determined by those skilled in the art, and may be adjusted according to various factors including a type of disease, severity of the disease, contents of other ingredients contained in the composition, a type of formulation, and an age, a weight, a general health status, a gender, and a diet of a patient, a dose time, a dose route, a secretion ratio of the composition, a treatment period, and simultaneously used drugs. It is important to include an amount capable of obtaining a maximum effect by a minimum amount without side effects by considering all of the factors. For example, in the composition of the present disclosure, 125 to 1000 µg/ml of the gintonin may be included.

Further, the present disclosure provides a method for prevention or treatment of ophthalmological diseases including administering a therapeutically effective amount of the gintonin of the present disclosure to mammals.

The term "mammals" used herein means mammals which are subjects for treatment, observation, or testing, and preferably, the humans.

In the treatment method of the present disclosure, in the case of adults, when administering the gintonin composition of the present disclosure once to several times a day, the gintonin included in the composition may include a concentration of 250 to 750 µg/ml.

In the treatment method of the present disclosure, the composition containing the gintonin of the present disclosure as an active ingredient may be administered by a general method through rectal, intravenous, intraarterial, intraperitoneal, intramuscular, intrasternal, percutaneous, topical, intraocular, or intradermal routes, but preferably, may be an eye liquid or injection.

A health functional beverage composition of the present disclosure is not particularly limited to other ingredients other than containing the gintonin as an essential ingredient at an indicated ratio and may further include various flavoring agents or natural carbohydrates like general beverages. In this case, the natural carbohydrates may include, for example, general sugars including monosaccharides such as glucose and fructose; disaccharides such as maltose and sucrose; and polysaccharides such as dextrin and cyclodextrin, and the like, and sugar alcohols such as xylitol, sorbitol and erythritol. Further, as the flavoring agents, natural flavoring agents (thaumatin, stevia extract, for example, rebaudioside A, glycyrrhizin, etc.) and synthetic flavoring agents (saccharin, aspartame, etc.) may be advantageously used. A ratio of the natural carbohydrate may be generally about 1 to 20 g and preferably about 5 to 12 g per 100 of the composition of the present disclosure.

Various advantages and features of the present disclosure and methods accomplishing thereof will become apparent from the following description of exemplary embodiments with reference to the accompanying drawings. Hereinafter, Examples of the present disclosure will be described in detail. Examples are to describe the present disclosure in detail and the scope of the present disclosure is not limited to Examples.

Example 1

Isolation of Crude Gintonin from Ginseng Roots Using Alcohol (Ethanol)

500 g of 4-year old white ginseng (*Panax ginseng* C. A. Meyer) powder purchased by the Korea Ginseng Corporation (Daejeon, Korea) was added with 80 to 100% (w/v) alcohol (ethanol) 5, extracted by reflux cooling at about 80 for 8 hrs, and filtered (the process was repeated three times), concentrated in a vacuum concentrator, dialyzed (a pore size of a dialysis membrane: 6,000 to 8,000), and then lyophilized to obtain 30 g of an ethanol extract.

The alcohol extract was dissolved in 20 mM Tris-HCl (pH 8.2) including 50% (w/v) ethanol and loaded in a DEAE sepharose anion-exchange resin column prefilled with the same solvent to sufficiently pass through an eluting solvent. In this case, as the eluting solvent, 20 mM Tris-HCl (pH 8.2) including 50% ethanol was used, and materials which were bound to the column, that is, ginsenoside without negative charges and the like or other low-molecular materials were sufficiently removed, and then the alcohol extract passed through the 20 mM Tris-HCl (pH 8.2) including 1M HCl and 50% (w/v) ethanol to collect materials bound to the anion-exchange resin column.

The materials collected in the column were dialyzed in a dialysis membrane having a pore size of 6,000 to 8,000 to remove the contained salt and ethanol and then lyophilized to obtain crude gintonin fractions 1,000 (yield: 0.2%).

In the ethanol extract (EtOH ext.), it is shown that an ingredient (CaCC is measured as 100 µg/ml) that weakly activates a $Ca^{2+}$ activated chloride channel (CaCC) endogenous to Xenopus oocytes is present and the crude gintonin having high CaCC activity (CaCC is measured as 1 µg/ml) may be easily isolated from the ethanol extract through simple chromatography. However, it is shown that unbound components to the anion-exchange resin have no CaCC activity (Korean Patent Registration No. 10-1305000).

Experimental Example 1

1-1. Culture of Human Corneal Epithelial Cell-T (HCE-T)

HCE-T cells (RCB-2280) were purchased from a Riken cell bank. The HCE-T cells were cultured in a medium in which 10% FCS was contained in a DMEM-Ham F12 (1:1) medium (Araki-sasaki et al., Investigative Ophthalmology and Visual Science 36, 614-621, 1995; Arakisasaki et al., J cellular Physiol. 182, 189-195, 2000).

1-2. Treatment of Corneal Injury Using Scratch Wound Healing Method

HCE-T ($2.5 \times 10^5$/well) was planted in a 24-well plate and cultured for 24 hrs and then cultured for 6 hrs in a 0.2% FBS-containing DMEM medium again. The wound was made by drawing a line through the center of each well where cells grew by using a 200-L pipette tip and then the floating cells were washed twice with a 1% FBS-containing DMEM medium to be removed.

The cells were treated with 0.03 to 1 μg/ml of gintonin and cultured and compared with cells without treating gintonin by observing and photographing (100×) cell shapes before and after gintonin treatment of each well with an inverted fluorescence microscope (AxioVert200; Carl Zeiss).

Figure 1:
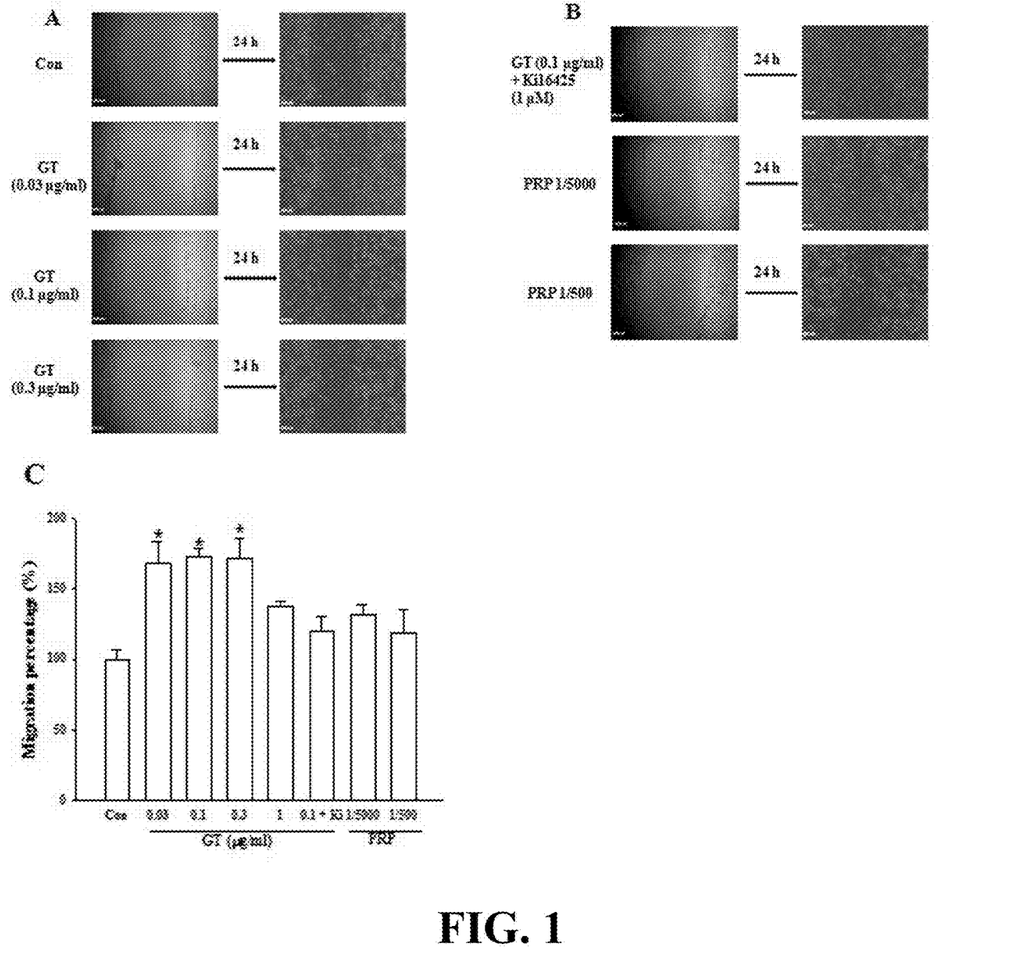
FIG. 1 is a photograph illustrating whether gintonin promotes in vitro cell migration in a test using human corneal epithelial-T (HCE-T) cells. In this case, FIG. 1 summarizes (A) an effect of gintonin at various concentrations on HCE-T cell migration, (B) an effect of LPA receptor antagonist on gintonin and effect of PRP on cell migration, and (C) an effect of gintonin and PRP on cell migration (*$p<0.01$, compared to control group (con)).

For the analysis of the degree of cell growth in a part wounded with the pipette tip, an area of the wound part where cells were not recovered was measured using Axio-Vision. As illustrated in FIG. 1A, in the case of the scratch wound, in a group without drug treatment, the scratching part was not filled after 24 hrs, but in the case of treating the gintonin, the cell migration action was increased for each dose concentration.

In the case of treating a LPA1/3 receptor antagonist, it was shown that the cell migration by the gintonin was inhibited, and when platelet rich plasma (PRP) was diluted 500 times and 5000 times, it was shown that the cell migration action was caused to treat the scratch wound. Further, it was illustrated in FIG. 1C that a result of treating the scratch wound in the HCE-T cell by the gintonin was summarized.

1-3. Mixture of Fura 2 and HCE-T Cells

In the present disclosure, it was shown that the gintonin stimulated the migration of wound healing of the HCE-T cells, and in order to verify whether the treatment of the gintonin in the HCE-T cells had an effect on a temporal increase in $[Ca^{2+}]_i$ in Fura 2-loaded mouse HCE-T cells, 2 to $4 \times 10^6$ cell/ml of HCE-T cell pretreated with Fura-2 were suspended in a 1.5 mM $Ca^{2+}$-containing buffer or a $Ca^{2+}$-free buffer, cultured at 37° C. for 10 minutes and then added with gintonin for each concentration to verify an effect on an intracellular calcium concentration in the HCE-T cells.

Particularly, according to a method such as Jrgensen and the like, HCE-T cells (1 to $2 \times 10^6$ cell/ml) were mixed in 2.5 M Fura 2-AM while being shaken for 30 minutes at a 37° C. incubator by using a $Ca^{2+}$-containing buffer (pH 7.4) consisting of NaCl 120 mM, KCl 5 mM, $MgCl_2$ 1 mM, $CaCl_2$ 1.5 mM, glucose 10 mM, and HEPES 25 mM and a $Ca^{2+}$-free buffer (pH 7.4) consisting of NaCl 120 mM, KCl 5 mM, $MgCl_2$ 1 mM, EGTA 0.2 mM, glucose 10 mM, and HEPES 25 mM, and an excessive amount of fura-2 was removed by washing the cells with the $Ca^{2+}$ buffer or the $Ca^{2+}$-free buffer three times.

1-4. Fluorescence Measurement of $[Ca^{2+}]_i$ in Cell Suspension $[Ca^{2+}]_i$ was estimated in the Fura 2-loaded cells by using a RF-5300PC intracellular ion measurement system (Shimadzu Corporation, Japan). Specifically, the Fura 2-loaded cells were finally diluted in 2 to $4 \times 10^6$ cells/ml of an experimental buffer and then transferred to a polystyrene cuvette (Elkay Ultra-UV). The cells were stirred by using a Teflon-coated magnet and the cuvet housing was adjusted to 37. Excitation wavelengths were alternated between 340 and 360 under a computer control and emission was detected at 510. In this case, the excitation and emission gap widths were set to 3 nm, and the background correction was performed according to a method of Jrgensen and the like, and digitonin and EGTA were used as a concentration adjustment reagent for fully combining fura-2 with $Ca^{2+}$ and making a state dissociated from $Ca^{2+}$.

1-5. Estimation of $[Ca^{2+}]_i$ from Fura 2 Measurement Value

A measured ratio value of 340:380 was converted to a value of $[Ca^{2+}]_i$ by using Equation of Hounsell and the like (Hounsell, E. F., Davies, M. J., and Smith, K. D. (1997) *Protein protocol handbook*, Humanna press, Totawa, 803-804).

$$[Ca^{2+}] = K_d[(R-R_{min})/(R_{max}-R)](S_{f380}/S_{b380})$$

Wherein, $K_d$ is a dissociation constant (224 nM), R is a measured fluorescence ratio of 340 nm: 380 nm, $R_{max}$ and $R_{min}$ are an R value at a saturated concentration added with 50 μg/ml of digitonin and an R value in a free medium added with 20 mM EGTA. Further, $S_{f380}$ and $S_{b380}$ are fluorescence intensity at 380 nm when adding digitonin and EGTA and the ratios are maximum and minimum values when these values are indicated (Grynkiewicz, G., M. Poenie, and R. Y. Tsien. (1985) *J Biol Chem* 260: 3440-3450).

1-6. Treatment for Glaucoma by Adjustment of Calcium ($Ca^{2+}$) Concentration $[Ca^{2+}]_i$)

It is known through recent documents and the like that glaucoma is caused by increase of intraocular pressure, and a calcium channel plays an important role in adjusting the intraocular pressure in the eyeballs. Further, it is reported that in lysophosphatidic acid (LPA), activity of receptors coupled with a GTP-binding protein (G protein), particularly, receptors connected to $G_{q/11}$ phospholipase C $IP_3$ $Ca^{2+}$ pathway protein kinase C (PKC) activity enhances a free calcium ($Ca^{2+}$) concentration $[Ca^{2+}]_i$ in the cells (Hwang et al., Mol Cells. 33(2):151-162, 2012). Further, it was reported that in some patients with normal TOP glaucoma, a use of a calcium channel blocker reduced a progression speed of the disease through relaxation of vasospasm.

The inventors verified whether to exhibit physiological/pharmacological main efficacy of the constituents of edible crude gintonin obtained from the ginseng using ethanol, found that in the process of studying the detailed chemical composition and its role, first, a large amount of lysophosphatidic acids (LPAs), particularly, LPA $C_{18:2}$, which are GPCR ligands with physiological/pharmacological activity in the ginseng was present, increased activity of free $Ca^{2+}$ in the cytoplasm was temporarily caused, and a stable form of sugar and protein that maintains the increased activity of free $Ca^{2+}$ in the cytoplasm as compared with free LPA was complex, and completed the present disclosure, and filed the patent (Korean Patent Application No. 10-2011-0744070, lysophosphatidic acid isolated and identified from ginseng and preparing method thereof).

Further, the inventors found that gintonin contained in edible crude gintonin obtained from ginseng using ethanol activated various kinds of LPA receptor subtypes with high affinity, completed the present disclosure, and filed the patent (Korean Patent Application No. 10-2011-0094194, use as natural medicinal plant-derived ligand of glycolipoprotein gintonin isolated and identified from ginseng). The gintonin also acts to activate the LPA receptors, but as one of features of the gintonin, it is shown that LPA $C_{18:2}$ is significantly more abundant than other LPAs (Korean Patent Application No. 10-2011-0744070, lysophosphatidic acid isolated and identified from ginseng and preparing method thereof).

The inventors verified that the gintonin activated the LPA receptors present in the cell membrane and the activation was performed through a signaling pathway connected to a signal transfer process that increased intracellular calcium through Gq/11 protein→PLC→$IP_3$ receptor→ER $Ca^{2+}$ reservoir→$Ca^{2+}$ release. Accordingly, according to the composition containing the gintonin, it is verified that a $Ca^{2+}$ calcium channel can be adjusted and the gintonin is used as a hyperosmolar agent for the treatment of glaucoma to treat glaucoma.

1-7. Treatment for Cataract by Adjustment of Calcium ($Ca^{2+}$) Concentration ($[Ca^{2+}]_i$)

Cataract is a disease in which the lens becomes hazy and does not pass the light properly and thus the field of vision becomes cloudy like the fog, congenital cataracts are mostly caused by unknown causes and may be caused by hereditary or prenatal infections (infections occurring in the fetus in the uterus), and metabolic abnormalities, and acquired cataracts are the most common age-related cataracts occurring with age and include cataracts caused by trauma, systemic diseases, and inflammation in the eyes.

However, it is known in many studies that calcium plays an important role in the formation of cataracts, and it is found that when the external calcium concentration falls below 1 mM, the transparency of the eyeballs is changed (Duncan G et al., Ciba Found Symp. 1984; 106:132-52. Richardson N L et al., The Journal of Nutrition [1985, 115(5):553-567], K. R. Hightower et al., Experimental Eye Research Volume 34, Issue 3, March 1982, Pages 413421). Accordingly, the inventors verified that when a $Ca^{2+}$ calcium channel is adjusted, the treatment of cataracts is possible.

1-8. Statistics

All data were compared by statistics between the control and experimental groups by using a Student's t-test. Statistical significance was considered at $p<0.05$. Animal test data were analyzed using a Newman-Keuls test and a one-way analysis of variance (ANOVA).

1-9. Effect of Promoting Cell Migration in HCE-T Cell

When scratch wounding was performed on cultured HCE-T cells and then gintonin was treated at different concentrations, the gintonin promoted migration of HCE-T cells at a low concentration (0.03 to 0.1 µg/ml), but the effect was reduced at 1 µg/ml (see FIG. 1). These experimental results showed that the action of the gintonin is effective at a concentration lower than 1 µg/ml. In order to verify whether the action of the gintonin is performed through LPA receptor activity, in the case of treating a LPA1/3 receptor antagonist Ki16425 before treatment of the gintonin, it is shown that the action of the gintonin is inhibited and the cell migration promotion by the gintonin is performed by the LPA receptor. Further, as a comparative experiment, it was also shown that even in the case of treating a diluted PRP, cell migration was promoted (FIG. 1C).

1-10. Effect of Increase in Intracytoplasmic Calcium in HCE-T Cells

The increase in intracytoplasmic calcium is known to be essential for wound healing and cell migration for wound healing (Chi and Trinkaus-Randall, J Cell Physiol. 228(5): 925-929, 2013). Therefore, as a result measuring a change in intracytoplasmic concentration of gintonin in HCE-T cells, it was shown that the gintonin increased the intracytoplasmic calcium concentration of HCE-T for each treatment concentration. It was shown that the concentration of intracytoplasmic calcium was increased at a concentration that promoted cell migration by the gintonin. In the case of treating 1 µg/ml of gintonin, a concentration of intracytoplasmic calcium is lower than the treatment at a lower concentration of gintonin, and it is caused by desensitization of the LPA receptor.

Figure 2:
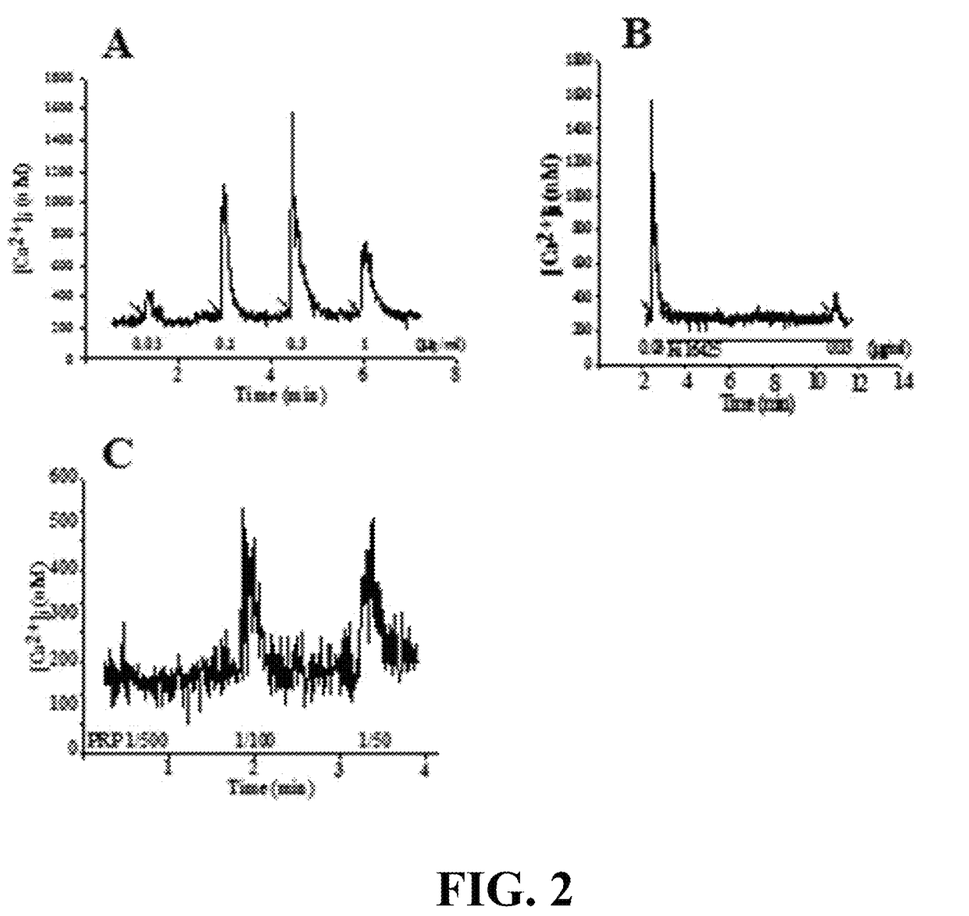
FIG. 2 is a photograph illustrating whether gintonin may temporarily increase a calcium concentration in the cytoplasm in human corneal epithelial-T (HCE-T) cells. In this case, FIG. 2 measures (A) a concentration-dependent effect, (B) an effect of Ki16425 as a LPA receptor antagonist, and (C) a change in calcium concentration in the cytoplasm by PRP.

It was shown that the increase in intracytoplasmic calcium by gintonin was blocked by the LPA1/3 receptor antagonist Ki16425 and the increase in intracytoplasmic calcium by gintonin was performed by the LPA receptor activity. It is shown that the PRP does not increase the intracytoplasmic calcium concentration at a dilution (1:500) concentration, which affects cell migration and only at a higher concentration, the PRP increases the intracytoplasmic calcium concentration which is lower than that of the gintonin (FIG. 2).

It is expected that the scratch wounding healing by the gintonin is caused by the increase in the intracytoplasmic calcium concentration, but the PRP has a possibility to be performed through a pathway regardless of the change in the intracytoplasmic calcium concentration. From the result, it was verified that the gintonin was effective in the treatment of glaucoma.

Experimental Example 2

2-1. Preparation of Experimental Animal 25 male New Zealand white rabbits of 1.6 to 2 kg were ordered. After the approval of the Experimental Animal Ethics Committee of Konkuk University, the experiment was performed as follows. Used reagents are as follows: 30 ml of saline (100 ml of sterilized physiological saline solution, Korea Pharmaceutical Industry Co., Ltd.), two 30 cc syringes, 100% alcohol, sterile cotton swabs, Telbit eye drop 3 mg/ml (oflxacin 3 mg/ml, 6 ml, eye drop antibiotic, Daewoo Pharm.), Alcaine eye drop 0.5% (proparacaine Hydrochloride 5 mg/ml, 15 ml, eye drop anesthetic solution, Korea Alcon), Fluorescein sodium ophthalmic strips (1 Strip/Pouch, 10 Pouches, Ophthalmology fluorescein staining reagent strip, Tianjin Jingming New Technological Development Co., Ltd, China), a slit lamp microscope (Hawk eye, Dioptrix, France), Amolis epithelial scrubber, cotton swabs, cotton gauze, gintonin for eye drop, and Solcorin eye drops 0.4 ml used in the related art (Hanlim Pharmaceuticals).

2-2. Concentration Analysis of Gintonin as Eye Drops Using Corneal Epithelial Injury Induction of Rabbit Eye Experimental groups are divided into five groups as follows. The groups are divided into five groups of a group non-treated with gintonin after corneal injury, a group treated with 125 µg/ml of gintonin after corneal injury, a group treated with 250 µg/ml of gintonin after corneal injury, a group treated with 500 µg/ml of gintonin, and a group treated with 1000 µg/ml of gintonin. After local anesthesia of the eyes, 100% alcohol is applied to the cornea for 20 seconds and then the epithelium of the cornea is completely removed by using an Amolis epithelial scrubber. Thereafter, a fluorescein test was performed on the cornea, and the area where the epithelium of the cornea was peeled off was observed, and then a fluorescein part was photographed by using a slit lamp microscope under cobalt blue light to ensure an image. After administration of eye drops (drug) a total of four times every 6 hours, fluorescein test was performed on the eye again to confirm the degree of regeneration of the epithelium of the cornea, and then photographed by using a slit lamp microscope under cobalt blue light to ensure an image of the treated cornea. The area of the cornea which was fluorescein-stained was measured using an Image Pro Plus program (Version 4.5.0.29, Media Cybernetics, Inc., Silver Spring, Md.) based on the photograph.

The area in which the corneal epithelium was healed was calculated by subtracting the area of the cornea which was fluorescein-stained after administration of the drug from the area of the cornea where the first fluorescein test was performed. After taking the fluorescence image, the rabbit was anesthetized with 1% 20 ml provision (propofol 10 mg/ml, intravenous general anesthesia, Myeongmun Pharmaceutical Co., Ltd.) and then authanized with KCl (KCl-40 inj., Dainhan Pharm Co. Ltd., Korea), and the eyes were extracted and fixed.

2-3. Comparison of Corneal Epithelial Regeneration Ability Using Induction of Corneal Epithelial Injury of Rabbit Eye Experimental groups are divided into three groups as follows. The groups are divided into a group non-treated with gintonin after corneal injury, a group treated with gintonin after corneal injury, and a group treated with Solcorin commercialized as a comparative drug with gintonin after corneal injury. A method of removing a corneal epithelium and a method of showing a regeneration degree of the epithelium used the above 2-1 method, after removing the corneal epithelium, the eye drops were taken a total of 12 times every 6 hours, after 72 hours, the degree of corneal regeneration was fluorescein-stained as shown in 2-1 above and a photograph was taken by a slit lamp microscope under cobalt blue light. Further, after taking the fluorescence image, the rabbit was anesthetized with 1% 20 ml provision (propofol 10 mg/ml, intravenous general anesthesia, Myeongmun Pharmaceutical Co., Ltd.) and then authanized with KCl (KCl-40 inj., Dainhan Pharm Co. Ltd., Korea), and the eyes were extracted and fixed.

Figure 3:
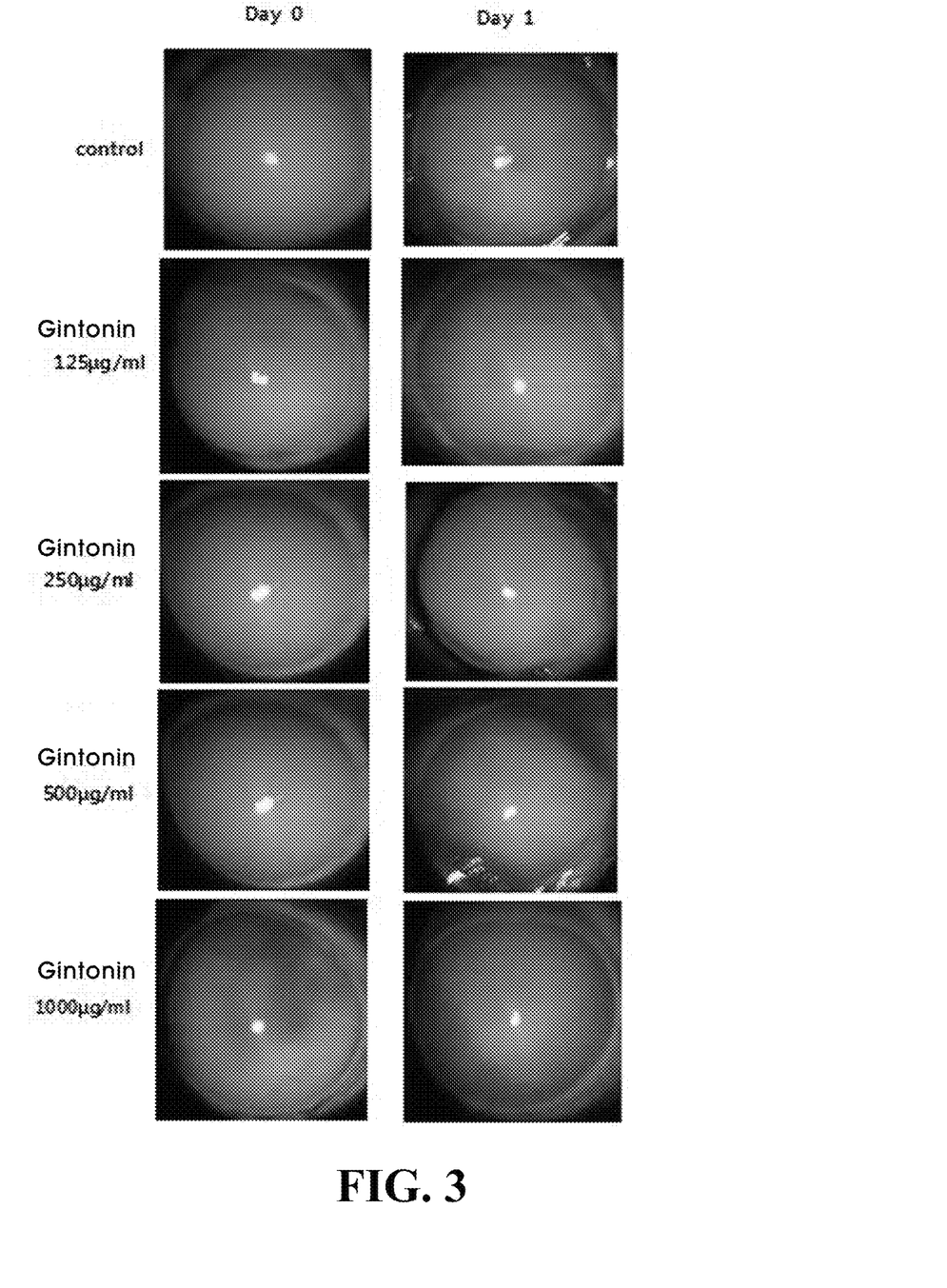
FIG. 3 is a photograph verifying a concentration of gintonin which is the most suitable for treatment of corneal injury in a test using rabbits.

2-4. Effect of Treatment for Corneal Injury According to Concentration of Gintonin in Experiment Using Rabbits In order to determine the most effective gintonin concentration for treatment, a concentration of gintonin capable of obtaining the best corneal healing effect by using the rabbit's cornea was determined. After the outer cover of the rabbit's cornea was removed and damaged, staining was performed using a fluorescent material, and as shown in FIG. 3, it was observed that the eyeballs were stained green as a whole. Thereafter, gintonin was administered 4 times a day to the cornea in 5 groups divided according to a concentration. After 24 hours, the area to be stained was confirmed by performed staining with fluorescent material and the area of the corneal epithelium was verified by subtracting the stained area after 24 hours from the first stained area. As a result, it was confirmed that the treatment effect was the best in the concentration group of 500 μg/ml (FIG. 3) and the results are summarized in Table 1.

Figure 4:
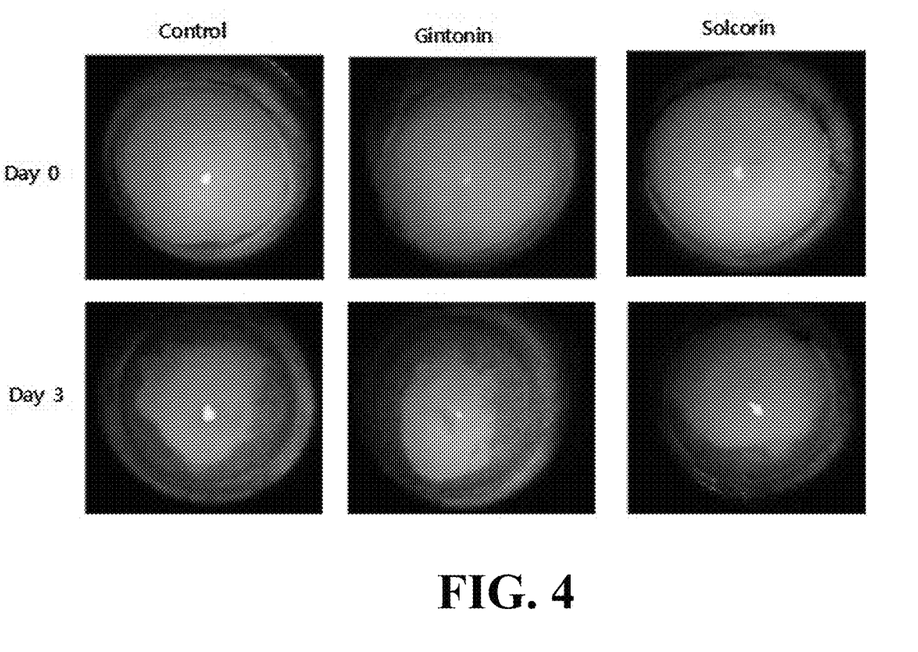
FIG. 4 is a photograph for a corneal injury treatment effect by 500 μg/ml of gintonin in a test using rabbits.

2-5. Comparison in Effect with Conventional Therapeutic Agent in Experiment Using Rabbits When the cornea of the rabbit is injured and the staining is performed using a fluorescent material, it can be observed that the eyeball is generally stained green as shown in FIG. 4. At this time, when the gintonin was administered compared with a group treated with physiological saline without administering the gintonin, it was observed that the area stained with a green fluorescent material after 3 days was significantly decreased statistically. Even in the case of administering Solcorin as a corneal injury healing agent which is currently used, a region stained by the fluorescent material was reduced compared to the group treated with only physiological saline (FIG. 4). Table 2 summarizes the experimental results using rabbits.

TABLE 2

Summary of implementation of treatment efficacy of gintonin after corneal injury in rabbits

| Treatment group | control group | gintonin treatment group (500 μg/ml) | solcorin treatment group |
| --- | --- | --- | --- |
| Average of Healing Area for 3 days treatments (any unit) | 394582.3 | 450463.8 | 412100.5 |

Healing size = pretreatment fluorescein staining area-postoperative fluorescein staining area (Healing size is a relative area value set in image pro) (Kim et al. Veterinary Ophthalmology 2009, 12:1, 36-42)

From the experimental result, it can be seen that when the composition containing gintonin was applied to cells or the eyes of the animal, the regeneration of the damaged cells progresses rapidly, and it was verified that the composition may be used as a therapeutic agent for ophthalmological diseases such as cornea, conjunctiva, and uvea. In addition, the gintonin is a glycolipoprotein and may be effectively used for xerophthalmia.

Experimental Example 3

Verification of Treatment Efficacy in Dogs with Corneal disease

The inventors actually performed the following experiment by targeting dogs with ophthalmological diseases in a veterinary clinic in order to verify treatment efficacy of gintonin in the dogs with ophthalmological diseases including ulcerative keratitis.

3-1. First Case

A photograph before using gintonin in a 9-year-old cocker spaniel dog with keratitis caused by surgical side effects after a nictitating membrane (3 eyelids) protrusion correc-

TABLE 1

Summary of implementation of treatment efficacy per concentration of gintonin after corneal injury in rabbits

| Treatment group | control group | gintonin (125 μg/ml) | gintonin (250 μg/ml) | gintonin (500 μg/ml) | gintonin (1000 μg/ml) |
| --- | --- | --- | --- | --- | --- |
| Average of Healing Area for 1 day treatments (any unit) | 84010.0 | 101469.5 | 130890.0 | 142642.0 | 141399.0 |

Healing size = pretreatment fluorescein staining area-postoperative fluorescein staining area (Healing size is a relative area value set in image pro) (Kim et al. Veterinary Ophthalmology 2009, 12:1, 36-42)

tion surgery (right and left eyes above) and a photograph after using gintonin (500 µg/ml of gintonin was dissolved in artificial tears (Lacure 5 ml)) for 4 days (right and left eyes below) were compared with each other.

Figure 5:
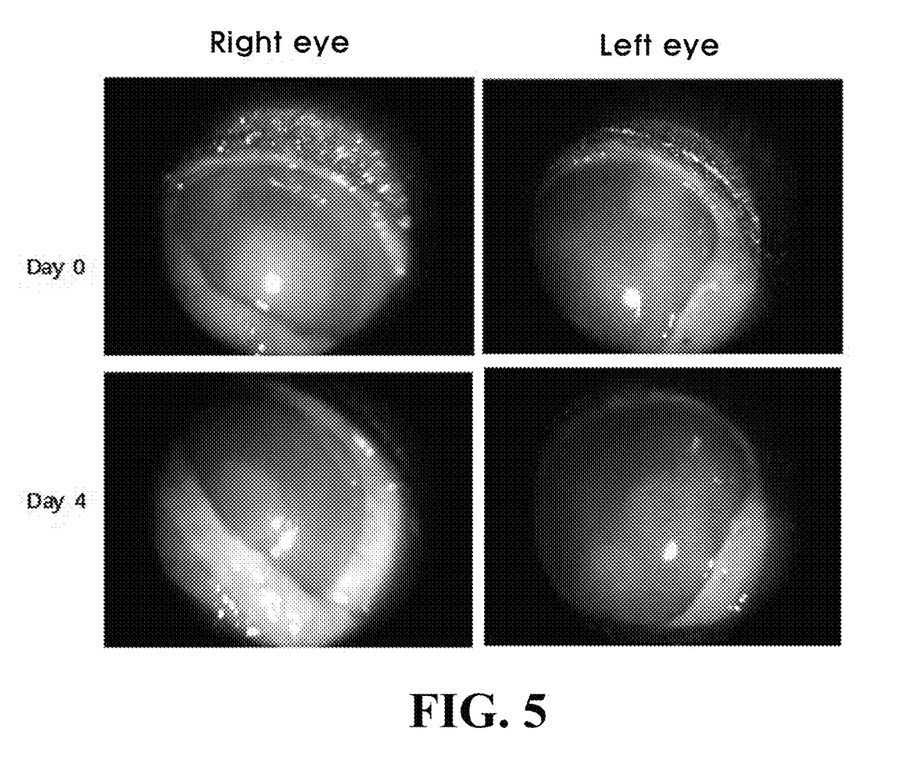
FIG. 5 is a photograph verifying a keratitis treatment effect according to treatment of 500 μg/ml of gintonin.

As illustrated in FIG. 5, at day 0, severe keratitis and corneal ulcer were shown. After applying antibiotics and gintonin for 4 days together with surgical treatment for 3 eyelids, keratitis symptoms were much improved and corneal erosion disappeared.

As the experimental result, it was verified that the treatment effect was remarkable in the eyes using gintonin.

3-2. Second Case

The inventors performed an experiment in order to verify an effect of gintonin by comparing a case using the gintonin and a case without using the gintonin in two cases with corneal ulcer. The case using gintonin was a 14-year-old dog (mix), after lens removal surgery due to lens dislocation, the eye was rubbed and corneal erosion occurred, and antibiotics and gintonin were administered. In the case without using the gintonin, antibiotics, artificial tears, and anticollagenase were prescribed and used in a 9-year-old poodle where corneal ulcers were caused by shampooing.

Figure 6:
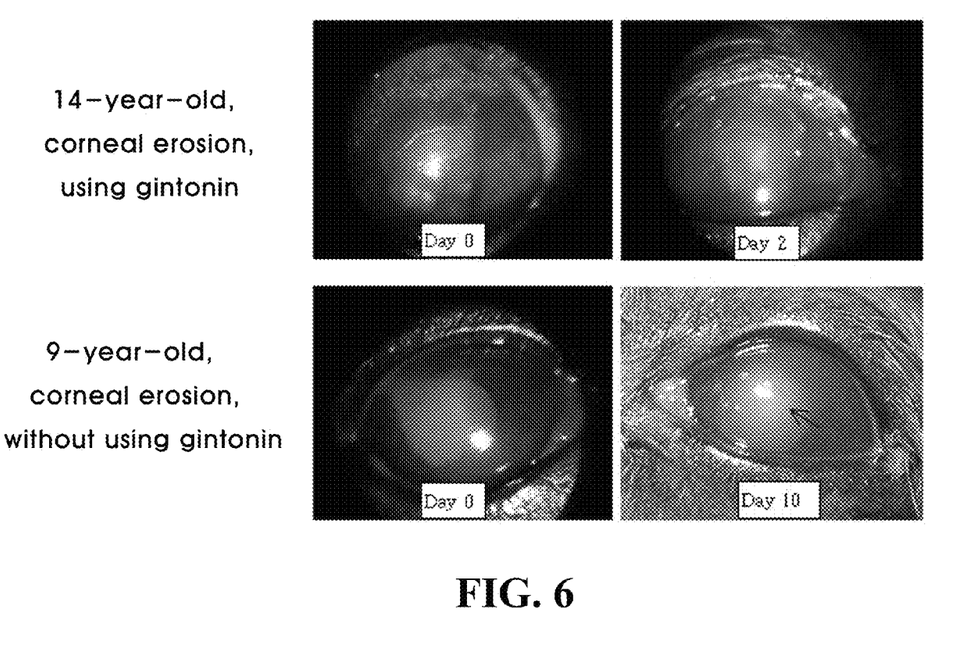
FIG. 6 is a photograph verifying a treatment effect of corneal ulcer according to treatment of gintonin by comparing an example using 500 μg/ml of gintonin and an example without using gintonin.

As the experimental result, as illustrated in an upper photograph in FIG. 6, in the case using gintonin, it can be seen that a region where fluorescence was stained at Day 0 and the stained region at Day 2 disappeared and corneal erosion disappeared.

As the experimental result, as illustrated in a lower photograph of FIG. 6, in the case without using the gintonin, even after 10 days, it was shown that the cornea was fluorescein-stained (arrow) and the eye was painful, and thus the corneal erosion was not treated (Day 10), and if the corneal ulcer is not treated quickly, delayed treatment is not a good condition because the corneal ulcer may have a great effect on eye sight, such as corneal opacity, neovascularization on the cornea, and the like in addition to astigmatism.

As the analyzed result, as seen in comparison of two cases, it can be seen that the gintonin has an excellent effect to reduce the duration of corneal ulcer treatment.

3-3. Third Case

Figure 7:
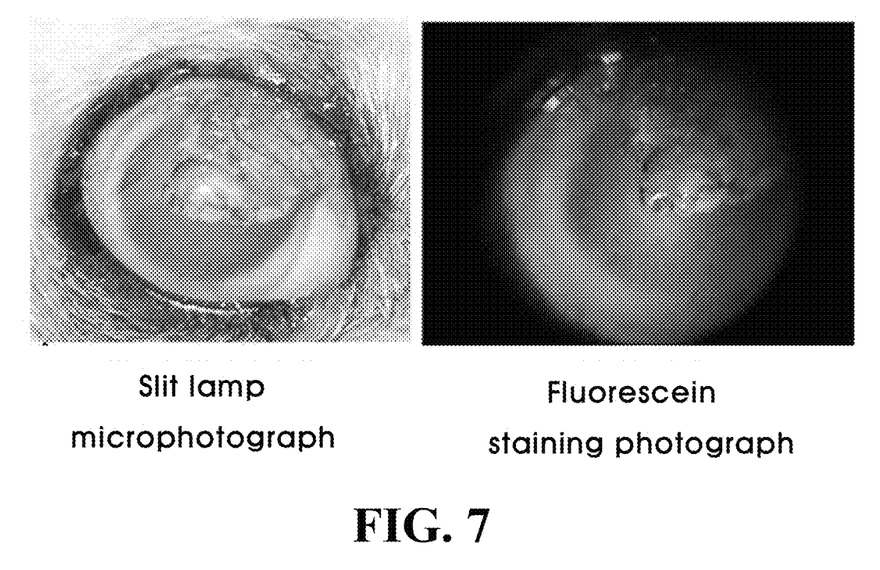
FIG. 7 is a photograph verifying that regeneration of anterior cornea is more promoted than a conventional method by treatment of 500 μg/ml of gintonin.

A 13-year-11-month-old Shih-Tzu dog was a patient with corneal edema due to posterior corneal cell degeneration and a patient enrolled by a secondary recurrent bullosa corneal ulcer and deep corneal ulcer due to chronic corneal edema as main symptoms. Thermokeratoplasty was performed with conjunctival flap transplantation and all epitheliums were removed by performing thermokeratoplasty. After surgery, gintonin and antibiotics were applied in the eyes four times a day. The present photograph is a photograph after 4 days after surgery, and in FIG. 7A, it is verified that a conjunctiva flap is very well grafted into the cornea and the blood vessels are well-developed, and in FIG. 7B, it can be seen that fluorescein test is performed, but staining was not performed due to epithelialization. According to conventional studies (Park et al. J Vet Clin 28, 533-537, 2011), it was reported that epithelial regeneration after thermokeratoplasty occurred after 11 days, but according to the experimental result, epithelialization was achieved only in 4 days.

3-4. Fourth Case

A 10-year-old Bosten teriior dog was a patient with chronic corneal edema due to dystrophia endothelialis cornea in the left eye and visited in the animal hospital and the chronic corneal edema was recurrent bullosa corneal ulcer as a main symptom. Thermokeratoplasty was performed in the patient's eye and anterior cornea was completely removed by applying alcohol during surgery and then the thermokeratoplasty was applied. After the surgery, gintonin and antibiotics were applied as eye drops and the present photograph is a photograph at a 6-th day after surgery.

Figure 8:
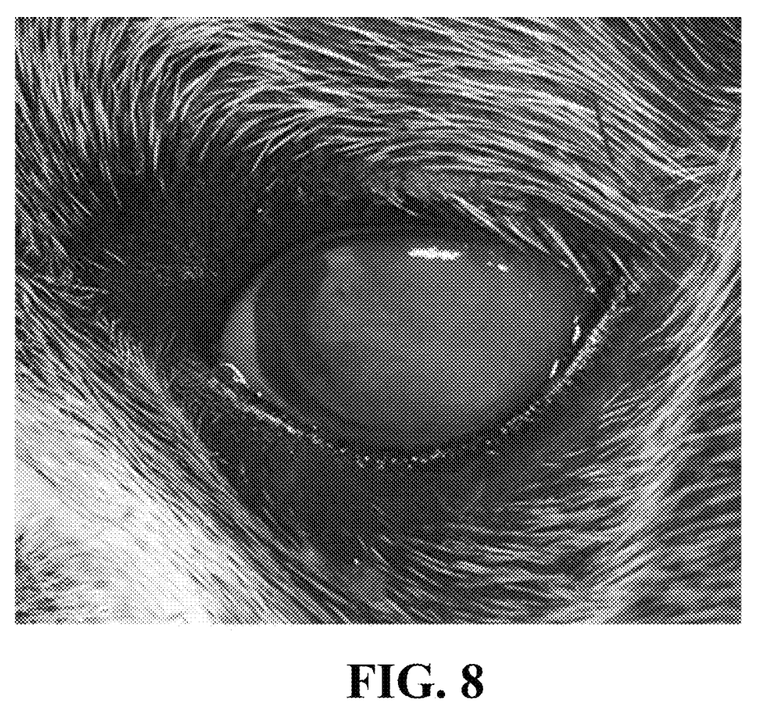
FIG. 8 is a photograph verifying that regeneration of anterior cornea is more promoted according to treatment of 500 μg/ml of gintonin than a conventional method.

As the experimental result, the fluorescein test was performed, but non-staining was verified and it can be seen that anterior cornea is regenerated based thereon. According to conventional studies (Park et al. J Vet Clin 28, 533-537, 2011), it was reported that 11 days or more was taken for completed regeneration of the anterior cornea after the surgery. However, after using the gintonin, it can be seen that the regeneration of the anterior cornea is much earlier (see FIG. 8).

3-5. Fifth Case

The present inventors compared the treatment progress by photographing a case of using gintonin and a case without using gintonin in two patients with corneal ulcer.

As the experimental result, as illustrated in FIG. 9A, it can be seen that a 13-year-old Maltese using antibiotics and gintonin was not stained by a fluorescein staining test on a 2-nd day (Day 2) after treatment for corneal ulcer (white arrow), and the regeneration of anterior cornea is almost performed.

As the experimental result, as illustrated in FIG. 9B, it can be seen that when viewing a photograph of a 5-year-old Shih-Tzu using only antibiotics and anti-antigen enzymes without using gintonin, it can be seen that on a 2-nd day after treatment (Day 2), staining was performed by a fluorescein staining test (black arrow), and thus regeneration of the anterior cornea had not yet been completed. Furthermore, this case shows that corneal ulcer is not treated properly and corneal ulcer is worse on the 10th day of treatment.

Figure 9:
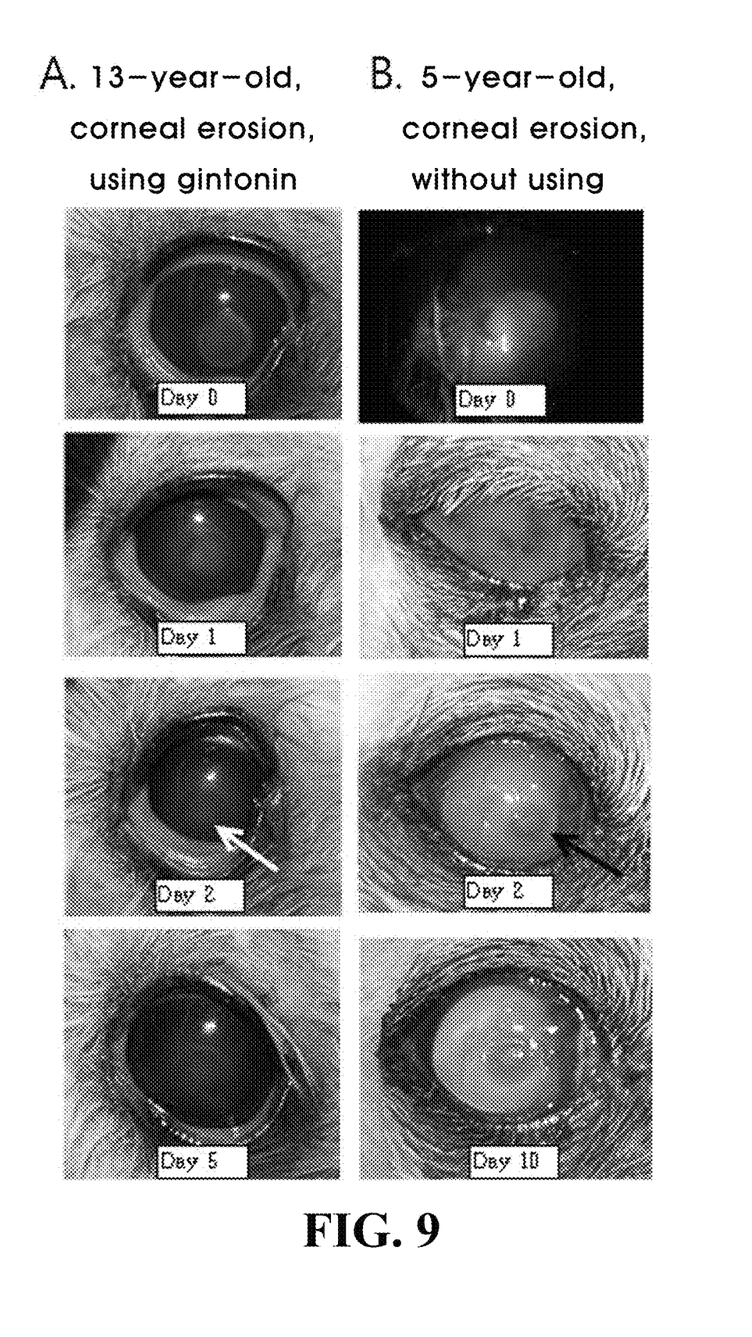
FIG. 9 is a photograph verifying a treatment effect of corneal ulcer according to treatment of gintonin by comparing an example using 500 μg/ml of gintonin and an example without using gintonin.

Accordingly, it can be seen that the treatment effect of gintonin for corneal ulcer is excellent (see FIG. 9).

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for treatment of a corneal disease, comprising administering an effective amount of a composition to a subject in need thereof, wherein the composition comprises a *ginseng* extract containing gintonin,
  wherein the *ginseng* extract is prepared by a method comprising:
    preparing an alcoholic extract by adding C1-C4 alcohol to *ginseng* root powder;
    collecting the alcoholic extract by using an anion-exchange resin;
    fractioning the collected alcoholic extract by a dialysis membrane having pore sizes of 6,000 to 8,000 to remove salt and alcohol; and
    lyophilizing the fractionated extract,
  wherein the composition contains 125 to 1000 µg/ml of gintonin, and
  wherein the corneal disease is selected from the group consisting of corneal erosion, corneal ulcer, or corneal injury.

2. The method for prevention or treatment of a corneal disease of claim 1, wherein the ginseng is one or more selected from the group consisting of red ginseng, fresh ginseng, white ginseng, cultivated ginseng, *panax ginseng*, wild ginseng, and ginseng and red ginseng byproducts.

3. The method for treatment of a corneal disease of claim 1, wherein the ginseng is one or more selected from the group consisting of *Panax ginseng, P. quiquefolius, P. notoginseng, P. japonicus, P. trifolium, P. pseudoginseng, P. vietnamensis*, and *Panax* quinquefolium.

4. The method for treatment of a corneal disease of claim 1, wherein the composition contains 250 to 750 µg/ml of gintonin.

5. The method for treatment of a corneal disease of claim 1, wherein the composition is an eye liquid or injection.

6. The method for treatment of a corneal disease of claim 1, wherein the gintonin activates Lysophosphatidic acid (LPA) receptors in cells.

7. The method for treatment of a corneal disease of claim 1, wherein the gintonin increases a concentration of free calcium ($Ca2+$) in the cytoplasm.

* * * * *